(12) United States Patent
Sun

(10) Patent No.: US 12,042,549 B2
(45) Date of Patent: Jul. 23, 2024

(54) PHOTOPOLYMERIZABLE RESIN COMPOSITIONS FOR DURABLE DENTAL PROSTHETIC AND RESTORATIVE ARTICLES

(71) Applicant: DENTSPLY SIRONA INC., York, PA (US)

(72) Inventor: Benjamin J. Sun, York, PA (US)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 17/213,642

(22) Filed: Mar. 26, 2021

(65) Prior Publication Data

US 2022/0304901 A1    Sep. 29, 2022

(51) Int. Cl.
| | |
|---|---|
| *A61K 6/62* | (2020.01) |
| *A61K 6/79* | (2020.01) |
| *A61K 6/891* | (2020.01) |
| *C08G 18/10* | (2006.01) |
| *C08G 18/48* | (2006.01) |
| *C08L 33/08* | (2006.01) |
| *C08L 33/14* | (2006.01) |

(52) U.S. Cl.
CPC .................. *A61K 6/62* (2020.01); *A61K 6/79* (2020.01); *A61K 6/891* (2020.01); *C08G 18/10* (2013.01); *C08G 18/4895* (2013.01); *C08L 33/08* (2013.01); *C08L 33/14* (2013.01)

(58) Field of Classification Search
CPC ...................................... A61K 6/887
See application file for complete search history.

(56) References Cited

U.S. PATENT DOCUMENTS

| | | | |
|---|---|---|---|
| 2014/0131908 A1* | 5/2014 | Sun .................. | B33Y 80/00 264/16 |
| 2016/0288376 A1* | 10/2016 | Sun .................. | A61C 13/0019 |
| 2016/0332367 A1* | 11/2016 | Sun .................. | C08L 33/08 |

* cited by examiner

*Primary Examiner* — Michael F Pepitone
(74) *Attorney, Agent, or Firm* — DENTSPLY SIRONA INC.

(57) ABSTRACT

The present invention relates to photopolymerizable resin compositions suitable for producing durable dental prosthetic and restorative articles. In particular, the invention relates to photopolymerizable resin compositions comprised of a specific combination of multiple polymerizable components, one or more resin-modifying particle components, and one or more photopolymerization initiator components. Compositions of the invention are especially well-suited to producing durable, stain-and wear-resistant dental prosthetic and restorative articles, such as artificial teeth, crowns, bridges, inlays, onlays, and veneers, in an efficient and reliable manner using additive manufacturing systems and methods (e.g., three-dimensional (3D) printing).

14 Claims, No Drawings

PHOTOPOLYMERIZABLE RESIN COMPOSITIONS FOR DURABLE DENTAL PROSTHETIC AND RESTORATIVE ARTICLES

FIELD OF THE INVENTION

The present invention relates to photopolymerizable resin compositions suitable for producing and/or repairing dental prosthetic and restorative articles, especially for long-term use as prosthetic teeth, crowns, bridges, inlays, onlays, and veneers. In particular, the invention relates to photopolymerizable resin compositions that are especially well-suited to producing durable, stain-resistant dental prosthetic and restorative articles that can be efficiently produced using additive manufacturing systems and methods (e.g., three-dimensional (3D) printing).

BACKGROUND

In the production of removable prosthetic dental appliances, such as full and/or partial dentures, or production of artificial teeth and fixed restorative dental articles, such as crowns, bridges, inlays, onlays, or veneers, a variety of material types have been developed and investigated over the years. Efforts have been directed to identifying materials that can satisfy both functional and aesthetic performance needs for repair or replacement of natural dentition in a cost-effective manner. In general, such material types usually have been selected from among alloys, ceramics or glass-ceramics, resin-modified ceramics, polymeric resin mixtures, and/or composite resin mixtures (e.g., polymeric resin reinforced with ceramic or other inorganic particles). Material selection for any given prosthetic or restorative article is often dependent on a variety of considerations (such as visual appearance/quality, durability, reliability, and cost of production) by dental professionals in consultation with their patients.

Some polymeric resin and/or composite resin compositions have been found to be particularly durable and well-suited to these applications, owing to their versatile properties (both in manufacturing and in use), biocompatibility, and relative cost-effectiveness. Historically, artificial teeth and/or restorative dental articles made from these compositions traditionally have been produced either by some version of a direct casting or injection molding process, or CNC (computer numerical control) milling process.

For teeth or restorative dental articles fabricated using direct casting or injection molding processes, uncured or partially cured (e.g., in flowable form, liquid, paste-like, or gel) polymeric resin or composite resin compositions may be poured, pressed, or injected into pre-formed molds of pre-determined shapes. This is followed by some application of controlled thermal and/or light treatment to induce final curing/hardening of the composition within the pre-formed mold. However, among the disadvantages or drawbacks for cast or injection molding processes are the extensive time, labor, and materials required to complete the molding process. Moreover, reliance on pre-formed molds of pre-determined shapes to accommodate a diverse range of tooth or restoration sizes for different patient needs has additional drawbacks. In particular, this often necessitates significant cost and time investment in fabrication and maintenance/replacement for an extensive inventory of different molds being available at all times for production.

For teeth or restorative dental articles fabricated using CNC milling processes, the general approach has been to use polymeric resin or composite resin compositions already fully cured in solid form to the shape of circular discs, blanks, or "pucks." Such cured resin discs are provided of sufficient diameter and thickness to accommodate subtractive formation of a plurality of teeth (anterior and/or posterior tooth forms) or restorative articles (e.g., crowns, bridges) from within the disc. Using CAD/CAM (computer-aided design/computer-aided manufacturing) software with CNC machining tools, a plurality of teeth or restorative articles can be cut out of these cured resin discs, in a very precise and reliable manner. However, the CNC milling process also has several disadvantages or drawbacks. For one, since this approach requires the machining of large, standardized pre-formed discs (to accommodate full range of small to large tooth sizes), there are many instances where it is not the most efficient use of either resin material or fabrication time. For example, in circumstances where only a few teeth, or restorative articles having comparatively small dimensions, are needed for a denture prosthesis or for restoring a patient's dentition, an extensive amount of material must be removed/cut-away from these discs. These material subtractions can easily amount to 90% or more of the total starting resin disc. As a consequence, this can lead to time-intensive processing times for the CNC milling device. Furthermore, the degree of wear for the respective milling tools is relatively high since the milling head is subjected to wear during processing of the blank, and so milling tools must be replaced at regular intervals. Moreover, the milled off material (the millings) must be disposed of or recycled.

More recently, there have been significant advances in the development of additive manufacturing (AM) technologies (also known as three-dimensional (3D) printing), in both apparatuses/systems and materials developed for these additive manufacturing processes. These technology advancements are now better enabling a transition from the more limited realm of mere 'rapid prototyping' of complex 3D objects, to the broader realm of reliable 'rapid production' for objects requiring critical functional performance in sustained use applications. Thus, efficient 'rapid production' of functionally reliable, high-quality dental articles by way of additive manufacturing is becoming a more attainable prospect for prosthetic dentistry. In particular, photopolymerizable fluid resin compositions can be prepared and loaded into programmable digitally-controlled light-based curing systems, such as SLA or DLP-based AM systems ("vat photopolymerization"), and/or material jetting systems (e.g., inkjet, MultiJet/PolyJet printing systems), where virtual designs of custom or bespoke denture bases, artificial teeth, and/or other dental restorative articles can be formed in a progressive layer-by-layer, dropwise, or continuous photo-curing manner. However, with respect to the photopolymerizable compositions, there remain deficiencies in chemical and/or physical property characteristics of compositions used for fabricating such long-term use dental articles. More specifically, many tradeoffs and challenges exist in establishing fluid resin compositions having advantageous "printability" behavior (e.g., good relative flow behavior for efficient layer-by-layer or continuous printing/build speeds, sufficient photoreactivity for photocuring ease or efficiency, and/or possessing consistent dimensional accuracy/integrity upon curing), while also being capable of delivering a variety of desirable final cured object properties (e.g., strength, toughness, and/or wear resistance for high durability and long-term reliability, biocompatibility, stain resistance, translucency, etc.).

For the foregoing reasons, there is a need to provide fluid resin compositions formulated particularly to meet the needs for 3D-printing artificial teeth and/or dental restorative articles (such as crowns, bridges, inlays, onlays, and veneers), especially those intended for long-term use in the oral cavity, in an efficient and reliable manner. It would be desirable, therefore, to have fluid resin compositions particularly well-suited and designed to provide versatile 3D-printable artificial tooth and/or dental restoration options as an effective alternative to traditional polymer pre-molded or CNC milled options.

SUMMARY

The present invention is directed to photopolymerizable resin compositions for the production and/or repair of dental prosthetic and/or restorative articles, especially when prepared using additive manufacturing systems and methods.

According to one embodiment of the invention, photopolymerizable compositions may comprise:

(a) at least about 45% by weight of one or more first polymerizable acrylic compounds, wherein the one or more first polymerizable acrylic compounds is a urethane di or multi(meth)acrylate derivative of 1,3-bis(isocyanatomethyl)cyclohexane characterized by one of the following formulas:

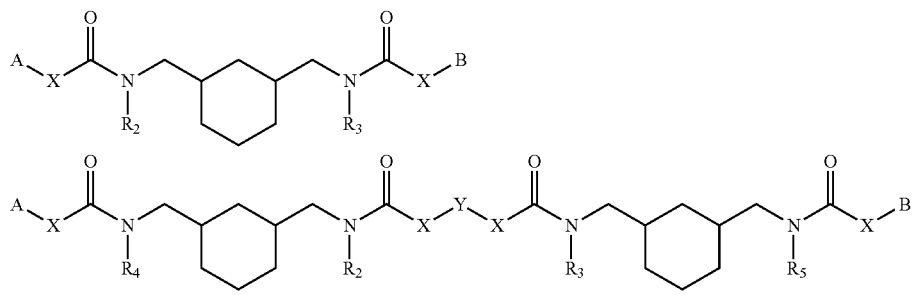

in which:

X is oxygen, nitrogen, or $NR_1$, where:

$R_1$ is hydrogen, a C1-C14 alkyl group, a C6-C14 cyclic group, C1-C14 cyclic alkyl group, a C6-C14 aromatic group, a C1-C14 aromatic alkyl group, or any combination thereof;

$R_2$, $R_3$, $R_4$ and $R_5$ is hydrogen, a C1-C14 alkyl group, a C6-C14 cyclic group, C1-C14 cyclic alkyl group, a C6-C14 aromatic group, a C1-C14 aromatic alkyl group, or any combination thereof;

Y is a C1-C14 alkyl group, a C6-C14 cyclic group, a C1-C14 cyclic alkyl group, a C6-C14 aromatic group, a C1-C14 aromatic alkyl group, or any combination thereof;

A and B independently of each other stand for one of the following formulas:

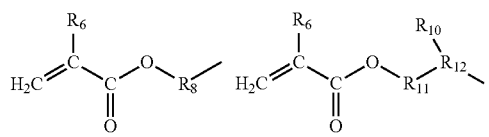

-continued

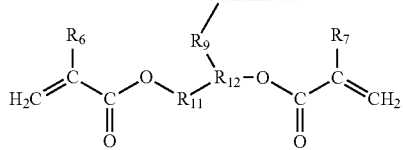

where:

$R_6$ and $R_7$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms;

$R_8$ and $R_9$ is a C1-C12 difunctional alkylene, a C1-C12 alkyl group, a C6-C12 cyclic group, a C1-C12 cyclic alkyl group, a C6-C12 aromatic group, a C1-C12 aromatic alkyl group, or any combination thereof, which can be interrupted by oxygen, sulfur, or otherwise atoms;

$R_{10}$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms;

$R_{11}$ represents a C1-C14 difunctional alkylene, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms; and $R_{12}$ represents a C1-C8 trifunctional alkyl group, which can be interrupted by oxygen, sulfur, or otherwise atoms:

(b) at least about 15% by weight of one or more second polymerizable acrylic compounds, the one or more second polymerizable acrylic compounds being different from the first polymerizable acrylic compounds;

(c) at least about 2% by weight of one or more third polymerizable acrylic compounds, wherein the one or more third polymerizable acrylic compounds is a methacrylate or acrylate compound prepared by reaction of a urethane pre-oligomer with an ethylenically unsaturated monomer;

(d) at least about 2% by weight of one or more resin-modifying particles; and (e) at least about 0.1% by weight of one or more photopolymerization initiators, wherein the total composition does not exceed 100% by weight.

In another aspect of the invention, the one or more third polymerizable acrylic compounds of the photopolymerizable resin composition may be the reaction product of a diisocyanate end-capped pre-oligomer intermediate compound with one or more hydroxyalkyl(meth)acrylate compounds.

In a further aspect of the invention, a diisocyanate end-capped pre-oligomer intermediate compound may be the reaction product of trimethyl-1,6-diisocyanatohexane with bisphenol A propoxylate.

In an embodiment, the weight ratio of first polymerizable acrylic compound(s) ($AC_1$) to third polymerizable acrylic compound(s) ($AC_3$), $AC_1:AC_3$, may be within the range of about 5:1 to about 20:1.

In another embodiment, the one or more resin-modifying particles of the photopolymerizable resin composition may be comprised of organic materials or organic-inorganic hybrid materials.

In a further embodiment, the one or more resin-modifying particles of the photopolymerizable resin composition may be selected from the group consisting of organic core-shell impact modifiers and organic-inorganic hybrid core-shell impact modifiers.

In accordance with another embodiment of the invention, the photopolymerizable resin composition may have a viscosity of no more than about 50,000 cP (50 Pa·s) at 25° C. in its uncured, fluid form.

In another embodiment, the photopolymerizable resin composition of the invention may have a Flexural Stress value of at least about 90 MPa in its cured, solid form, using additively manufactured test specimen bars that are prepared and then measured in accordance with ISO 20795-1:2013.

In still another embodiment, the photopolymerizable resin composition of the invention may have a Flexural Modulus value of at least about 2300 MPa in its cured, solid form, using additively manufactured test specimen bars that are prepared and then measured in accordance with ISO 20795-1:2013.

In still another embodiment, the photopolymerizable resin composition of the invention may have a Fracture Toughness value ($K_{max}$) of at least about 0.90 MPa·m$^{1/2}$ in its cured, solid form, using additively manufactured test specimen bars that are prepared and then measured in accordance with ISO 20795-1:2013.

In still another embodiment, the photopolymerizable resin composition of the invention may have a Work of Fracture value ($W_f$) of at least about 90 J/m$^2$ in its cured, solid form, using additively manufactured test specimen bars that are prepared and then measured in accordance with ISO 20795-1:2013.

In yet another embodiment, the photopolymerizable resin composition of the invention may have a Localized Wear Volume Loss of no more than about 0.15 mm$^3$ in its cured, solid form, using additively manufactured test specimen bars that are prepared and then measured in accordance with the In-Vitro Localized Wear method.

DETAILED DESCRIPTION

In the Summary above, and in the Detailed Description and Claims presented below, reference is made to particular features and embodiments of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The following additional definitions shall apply throughout the specification and claims of the invention, unless specifically indicated otherwise.

The term "about" is used herein as a term of approximation to mean plus or minus 5 percent of the specified value, preferably plus or minus 3 percent of the specified value, more preferably plus or minus 1 percent of the specified value.

The terms "essentially" and "substantially" are used herein as terms of approximation to denote in large part, but not necessarily wholly or perfectly, in relation to the fundamental nature or predominant characteristic being described.

The term "at least" followed by a number is used herein to denote the start of a range beginning with that number (which may be a range having an upper limit or no upper limit, depending on the variable being defined). For example, "at least 1" means 1 or more than 1.

The terms "at most" or "no more than" followed by a number is used herein to denote the end of a range ending with that number (which may be a range having 1 or 0 as its lower limit, or a range having no lower limit, depending upon the variable being defined). For example, "at most 100" or "no more than 100" means 100 or less than 100. When, in this specification, a range is given as "(a first number) to (a second number)" or "(a first number)-(a second number)," this means a range whose lower limit is the first number and whose upper limit is the second number. For example, 1 to 5 mm means a range whose lower limit is 1 mm, and whose upper limit is 5 mm.

The term "and/or," as used herein, includes any and all possible combinations of one or more of the associated listed items, as well as the lack of combination when interpreted in the alternative ("or"). For example, "A and/or B" means A alone, B alone, or A and B together or mixtures thereof.

Descriptions presented herein provide explanations and illustrative examples of improved photopolymerizable resin compositions suitable for producing and/or repairing dental restorative and prosthetic articles, especially for long-term use as prosthetic teeth, crowns, bridges, inlays, onlays, and veneers. Photopolymerizable resin compositions according to one or more embodiments of the invention may comprise a specific combination of multiple polymerizable components, one or more resin-modifying particle components, and one or more photopolymerization initiator components. Disclosure of the particular aspects or features for each of these components is provided in the following specification and claims.

Polymerizable Components

Compositions of the invention include a combination of polymerizable components. In an embodiment, the composition may include: (a) one or more first polymerizable acrylic compounds that is a urethane di(meth)acrylate, or multi(meth)acrylate, derivative of an (isocyanatomethyl) cyclohexane, (b) one or more second polymerizable acrylic compounds, different from the one or more first polymerizable acrylic compounds, and (c) one or more third polymerizable acrylic compounds that is a methacrylate or acrylate compound prepared by reaction of a urethane pre-oligomer with an ethylenically unsaturated monomer.

In one embodiment, the combination of first and third polymerizable acrylic compounds included in the composition may be at least about 50%, preferably at least about 55%, and no more than about 80%, preferably no more than about 75%, by weight of the total composition.

In another embodiment, the combination of first, second, and third polymerizable acrylic compounds included in the composition may be at least about 70%, preferably at least about 75%, and no more than about 97%, preferably no more than about 95%, by weight of the total composition.

First Polymerizable Acrylic Compound(s)

Compositions of the invention include one or more first polymerizable acrylic compounds described herein below. In particular, one or more first polymerizable acrylic compounds of the invention may be included in an amount of at least about 45%, and preferably at least about 50%, by weight of the total composition. In an embodiment, one or more first polymerizable acrylic compounds may be included in an amount of no more than about 75%, and preferably no more than about 70%, by weight of the total composition. It has been observed that by including at least about 45% by weight of the first polymerizable acrylic compound in compositions of the invention, particularly desirable levels of final cured resin strength, toughness and/or wear property values can be attained that are well-suited for dental restorative and prosthetic articles, especially for long-term use as prosthetic teeth, crowns, bridges, and the like.

Preferably, the one or more first polymerizable acrylic compounds is a urethane di(meth)acrylate derivative of an (isocyanatomethyl)cyclohexane (e.g., 1,3-bis(isocyanatomethyl)cyclohexane) that may be selected from compounds characterized by one of the following formulas:

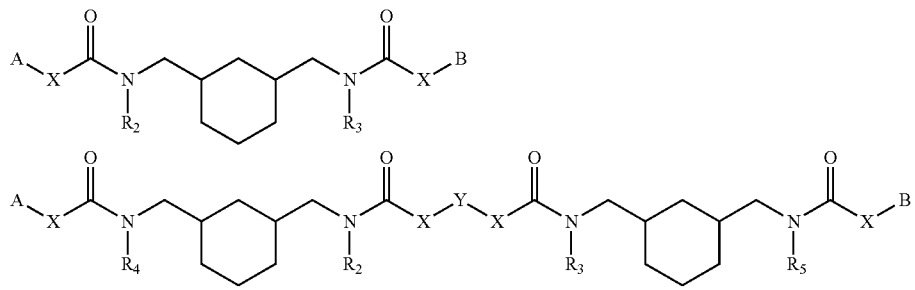

in which:
X is oxygen, nitrogen, or NR1, where R1 is hydrogen, a C1-C14 alkyl group, a C6-C14 cyclic group, C1-C14 cyclic alkyl group, a C6-C14 aromatic group, a C1-C14 aromatic alkyl group, or any combination thereof;
R2, R3, R4 and R5 is hydrogen, a C1-C14 alkyl group, a C6-C14 cyclic group, C1-C14 cyclic alkyl group, a C6-C14 aromatic group, a C1-C14 aromatic alkyl group, or any combination thereof;
Y is a C1-C14 alkyl group, a C6-C14 cyclic group, a C1-C14 cyclic alkyl group, a C6-C14 aromatic group, a C1-C14 aromatic alkyl group, or any combination thereof. Examples of Y include as 1,3-cyclohexanedimethylene, 1,4-cyclohexanedimethylene, or otherwise;
A and B independently of each other stand for:

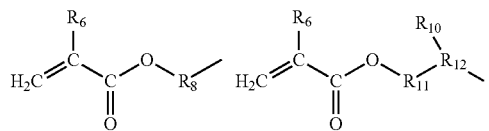

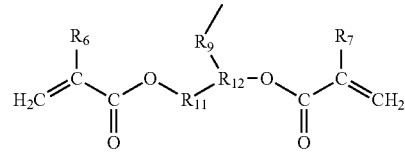

where:
$R_6$ and $R_7$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms;

$R_8$ and $R_9$ is a C1-C12 difunctional alkylene, a C1-C12 alkyl group, a C6-C12 cyclic group, a C1-C12 cyclic alkyl group, a C6-C12 aromatic group, a C1-C12 aromatic alkyl group, or any combination thereof, which can be interrupted by oxygen, sulfur, or otherwise atoms;

$R_{10}$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms:

$R_{11}$ represents a C1-C14 difunctional alkylene, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms; and $R_{12}$ represents a C1-C8 trifunctional alkyl group, which can be interrupted by oxygen, sulfur, or otherwise atoms.

It is contemplated that A, B, X, Y, $R_1$, $R_2$, $R_3$, $R_4$, $R_5$, $R_6$, $R_7$, $R_8$, $R_9$, $R_{10}$, $R_{11}$, $R_{12}$, or any combination thereof may be further inserted, substituted or non-substituted. When inserted or substituted, possible substituents may include, but are not limited to, one or more of the groups halogen, O, S, NH, CO—NH, NH—CO, NH—CO—O, O—CO—NH, NH—CO—NH, —OCH$_3$, —OH, —CN, —NO$_2$, —COOH, —COOCH$_3$, or any combination thereof, though not required.

Furthermore, urethane di(meth)acrylate derivatives in which A and B have the same meaning are preferred.

Particularly preferred non-limiting urethane di(meth)acrylate derivatives may include:

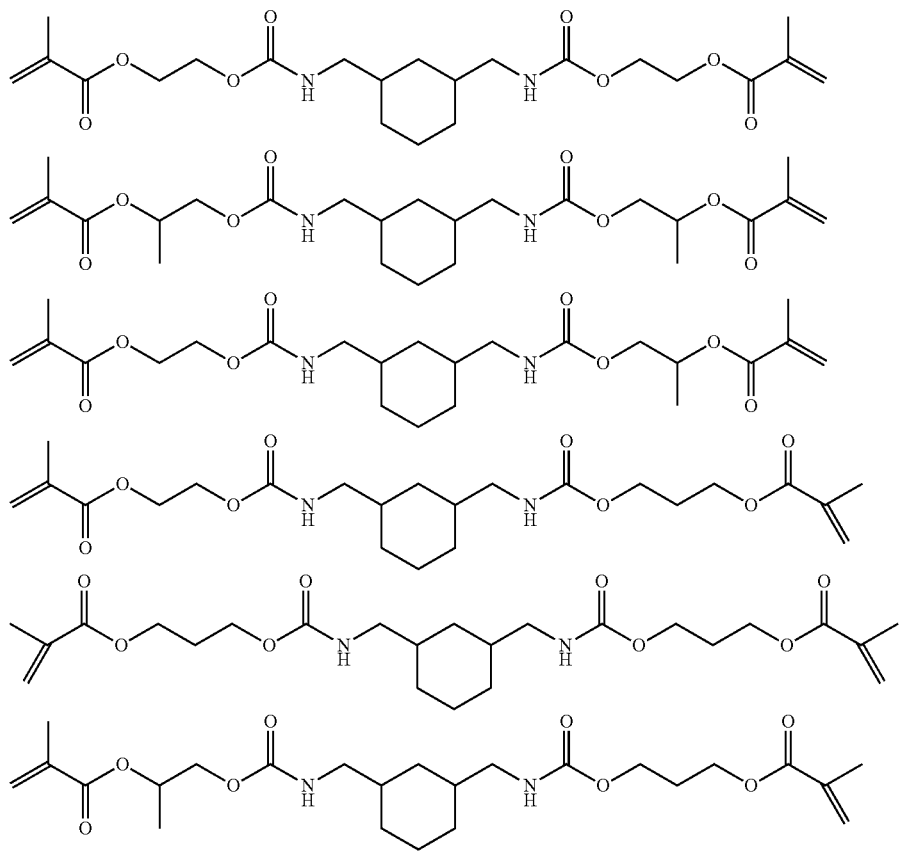
Other particularly preferred urethane di(meth)acrylate derivatives may include:
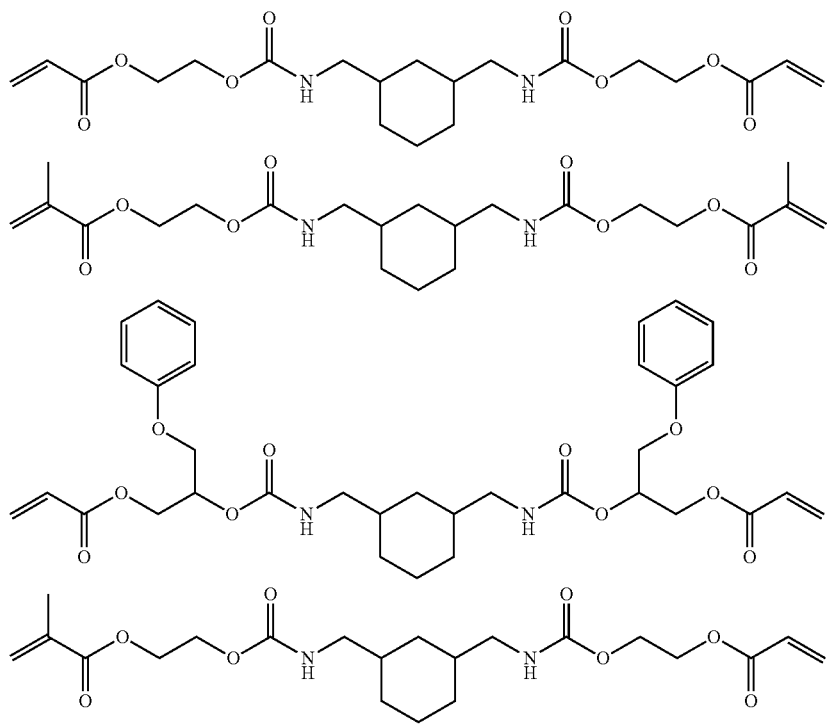

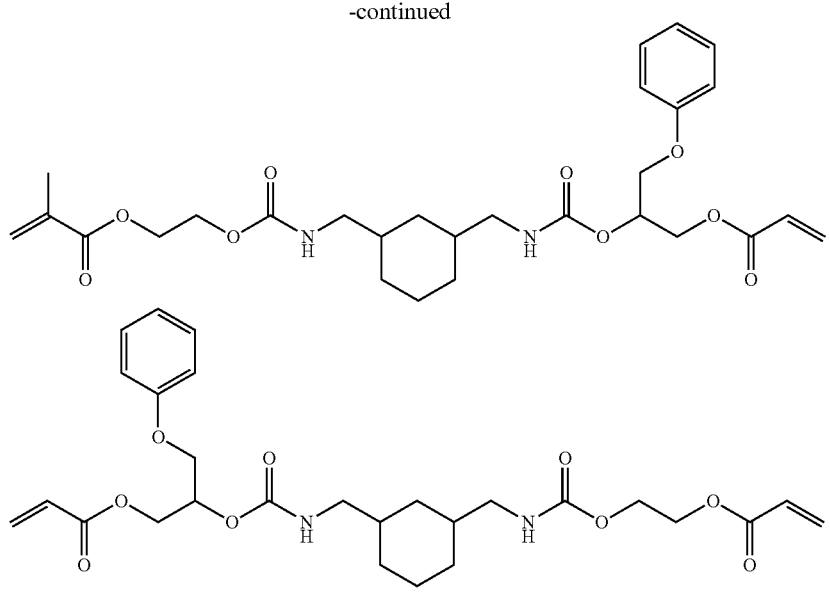

The urethane di(meth)acrylate derivatives according to the invention can be prepared as disclosed below in Examples 1 to 6, Second Polymerizable Acrylic Compound(s)

Compositions of the invention may further include one or more second polymerizable acrylic compounds, different from the first polymerizable acrylic compound. In particular, these one or more second polymerizable acrylic compounds of the invention may be included in an amount of at least about 15%, preferably at least about 20%, by weight of the total composition. In an embodiment, one or more second polymerizable acrylic compounds may be included in an amount of no more than about 45%, preferably no more than about 40%, by weight of the total composition. Second polymerizable acrylic compounds of the invention may be ethylenically unsaturated monomers capable of free-radical polymerization with the first polymerizable acrylic compound, and may include any combination of the polymerizable acrylic compounds discussed herein below. One or more of these second polymerizable acrylic compounds may be chosen, and used alone and/or in different combinations and proportions, to modify various desired properties of the fluid resin composition and/or final cured resin composition. Such properties may include fluid resin viscosity, thermal stability, polymerization rate, cured resin mechanical strength/toughness and flexibility, cured resin dimensional integrity (e.g., low percent shrinkage), biocompatibility, stain resistance, color, and translucency.

The one or more second polymerizable acrylic compounds that may be used in compositions of this invention include, but are not limited to, mono-, di- or poly-acrylates and methacrylates such as methyl acrylate, methyl methacrylate, methacrylic acid, ethyl acrylate, ethyl methacrylate, isopropyl methacrylate, tert-butyl (meth)acrylate, cyclohexyl (meth)acrylate, 4-tert-butylcyclohexyl (meth) acrylate, 3,3,5 trimethylcyclohexyl methacrylate, tetrahydrofurfuryl (meth)acrylate, n-hexyl acrylate, 2-phenoxyethyl (meth)acrylate, stearyl acrylate, allyl acrylate, isobornyl (meth)acrylate, stearyl (meth)acrylate, phenoxy benzyl (meth)acrylate, o-phenylphenol ethyl (meth)acrylate, tris(2-hydroxy ethyl)isocyanurate diacrylate, the reaction product of octadecyl isocyanate and 2-hydroxyethyl methacrylate, the reaction product of octadecyl isocyanate and caprolactone 2-(methacryloyloxy)ethyl ester, the reaction product of octadecyl isocyanate and 2-hydroxyethyl acrylate, the reaction product of octadecyl isocyanate and hydroxypropyl (meth)acrylate, the reaction product of octadecyl isocyanate and 2-hydroxypropyl 2-(methacryloyloxy) ethyl phthalate, the reaction product of octadecyl isocyanate and 2-hydroxy-3-phenoxypropyl acrylate, the reaction product of octadecyl isocyanate and glycerol dimethacrylate, the reaction product of octadecyl isocyanate and pentaerythritol triacrylate, the reaction product of cyclohexyl isocyanate and 2-hydroxyethyl (meth)acrylate, the reaction product of benzyl isocyanate and 2-hydroxyethyl (meth)acrylate, 1,14-tetradecanedimethacrylate, dimethylol tricyclodecane diacrylate, glycerol di(meth)acrylate, glycerol tri(meth)acrylate, ethylene glycol di(meth)acrylate, diethyleneglycol di(meth)acrylate, triethyleneglycol di(meth)acrylate, tetraethylene glycol di(meth)acrylate. 1,3-propanediol di(meth) acrylate, trimethylolpropane tri(meth)acrylate, 1,2,4-butanetriol trimethacrylate, 1,4-cyclohexanediol dimethacrylate, 1,6-hexanediol dimethacrylate, pentaerythritol tri(meth) acrylate, pentaerythritol tetra(meth)acrylate, sorbitol hexacrylate, 2,2-bis[4-(2-acryloyloxyethoxy)phenyl]propane, 2,2-bis[4-(methacryloyloxyethoxy)phenyl]propane (or ethoxylated bisphenol A dimethacrylate) (EBPADMA), 2,2-bis[4-(2-hydroxy-3-acryloyloxypropoxy)phenyl]propane, 2,2-bis[4-(2-hydroxy-3-methacryloyloxypropoxy)phenyl] propane (Bis-GMA); the reaction product of Bis-GMA and octadecyl isocyanate, the reaction product of Bis-GMA and cyclohexyl isocyanate, urethane dimethacrylate (UDMA), diurethane dimethacrylate (DUDMA), 4,13-dioxo-3,14dioxa-5,12-diazahexadecane-1,16-diol diacrylate, 4,13-dioxo-3,14 dioxa-5,12-diazahexadecane-1,16-diol dimethacrylate 4,19-dioxo-3,20 dioxa-5,18-diazahexadecane-1,22-diol diacrylate, 4,19-dioxo-3,20 dioxa-5,18-diazahexadecane-1,22-diol dimethacrylate, the reaction products of 2-isocyanatoethyl methacrylate and diols, polyurethane dimethacrylate (PUDMA), alkoxylated pentaerythritol tetraacrylate, polycarbonate dimethacrylate (PCDMA), the bis-acrylates and bis-methacrylates of polyethylene glycols, (meth)acrylate modified silicones, light curable epoxides, epoxy methacrylate (or acrylate), copolymerizable mixtures of acrylated monomers and acrylated oligomers, as well as combinations and/or mixtures thereof.

Third Polymerizable Acrylic Compound(s)

Compositions of the invention may further include one or more third polymerizable acrylic compounds described herein below. In particular, one or more third polymerizable acrylic compounds of the invention may be included in an amount of at least about 2%, preferably at least about 3%, and more preferably at least about 4%, by weight of the total composition. In an embodiment, one or more third polymerizable acrylic compounds may be included in an amount of no more than about 20%, preferably no more than about 18%, and more preferably no more than about 15%, by weight of the total composition. Surprisingly, it has been discovered that by including at least about 2% by weight of a third polymerizable acrylic compound in compositions of the invention, final cured resin strength, toughness and/or wear properties can be substantially improved in comparison to compositions where such third polymerizable acrylic compound is either included in amounts less than about 2%, or excluded entirely.

In a further embodiment, the weight ratio of first polymerizable acrylic compound(s) to third polymerizable acrylic compound(s) (herein also simply designated as the weight ratio of $AC_1:AC_3$ for convenience) may be within the range of about 5:1 to about 20:1. In a further preferred embodiment, the weight ratio of $AC_1:AC_3$ may be within the range of about 6:1 to about 15:1.

More specifically, the one or more third polymerizable acrylic compounds may include methacrylate (or acrylate) compounds prepared by reaction of a urethane pre-oligomer with an ethylenically unsaturated monomer, such as a hydroxylalkylmethacrylate. Preferably such polymerizable acrylic compounds include a structure within the scope of at least one of general formulas I to V below.

In a preferred embodiment, the urethane pre-oligomer is linear, comprises isocyanate end groups and has a structure within the scope of general formula I:

$$\text{OCN—(R}_1\text{—NH—CO—O—R}_2\text{—O—OC—NH)}_m\text{-R}_1\text{—NCO} \qquad \text{I}$$

wherein $R_1$ and $R_2$ are either an alkyl having from 1 to 14 carbon atoms or containing at least an aromatic group having from 6 to 14 carbon atoms, m is an integer from 0 to 20, the value of m in the oligomer depends on the molar ratio of diisocyanate to diol used, and the value of m increases as this molar ratio decreases. The diisocyanate portion has the structure OCN—$R_1$—NCO and the diol portion has the structure HO—$R_2$—OH.

In another preferred embodiment, the urethane pre-oligomer is formed by reaction of at least one diol in excess, and at least one diisocyanate to yield a urethane pre-oligomer having a structure within the scope of one or more of general formulas II to IV.

General Formulas II to IV:

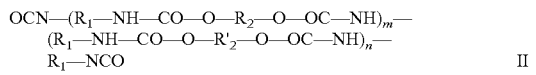
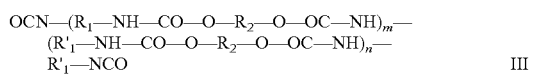
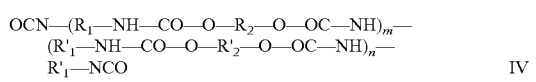

wherein $R_1$, $R'_1$, $R_2$ and $R'_2$ each independently is an alkyl having from 1 to 14 carbon atoms or at least an aromatic group having from 6 to 14 carbon atoms, n and m are each independently integers from 0 to 20, the sum of n and m in the oligomer depends on the molar ratio of diisocyanates to diols used, and the value of the sum of n and m increases as this molar ratio decreases. The diisocyanates have the structures OCN-$R_1$-NCO and OCN-$R'_1$—NCO and the diols have the structures HO—$R_2$—OH and HO—$R'_2$—OH. The more complex structures of urethane pre-oligomer are constructed from at least two different diols and at least two different diisocyanates.

In another preferred embodiment, reaction of the urethane pre-oligomer with an ethylenically unsaturated monomer, as described further below, yields a polymerizable compound having the structure within the scope of the general formula V:

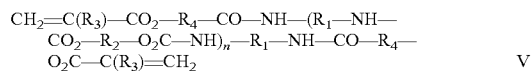

wherein $R_3$ is hydrogen, or an alkyl, such as a methyl group, and $R_4$ is an alkyl group having from 1 to 14 carbon atoms, and n is an integer from 0 to 20. A typical ethylenically unsaturated monomer is a hydroxyalkyl (meth)acrylate, e.g., 2-hydroxyethyl methacrylate, hydroxypropyl methacrylate, caprolactone 2-(methacryloyloxy) ethyl ester, and the like.

Preferred mechanical properties of cured resin and the desired handling properties of compositions may be present when the value of n in the compound is not greater than 10; more preferably n is not greater than 5. The preferred value of n in the compound largely depends on the requirements of the specific application. The most preferable value of n in the compound for aromatic ring based diol is between 1 and 3. Therefore, the molar ratio of diisocyanate to diol for aromatic ring based diol is most preferable between 1.33 and 2. The most preferable value of n in the compound for alkyl based diol is between 1 and 4. Therefore, the molar ratio of diisocyanate to diol for alkyl based diol is most preferable between 1.25 and 2.

Catalysts known in the art may be used to accelerate the formation of the isocyanate-ended pre-oligomer and end-capped ethylenically unsaturated monomer, for example, tertiary amines and metal salts, e.g. stannous octoate and in particular dibutyl tin dilaurate. Preferred stabilizers used in this invention are butylated hydroxytoluene (BHT) and the methyl ether of hydroquinone (MEHQ).

Examples of diisocyanates useful for making urethane pre-oligomers of the invention include trimethyl-1,6-diisocyanatohexane, 1,6-diisocyanatohexane. 1,8-diisocyanatooctane, isophorone diisocyanate, 4,4'-methylenebis(cyclohexyl isocyanate), cyclohexyl diisocyanate, 3-methylhexane-1,6-diisocyanate, 3-ethyl-1,6-hexanediisocyanate, 5-methyl-1,9-nonanediisocyanate, 5-ethyl-1,10-decanediisocyanate, 2,3-dimethyl-1,6-hexanediisocyanate, 2,4-dimethyl-1,8-octanediisocyanate, 2,4,6-trimethyl-1,7-heptanediisocyanate, 2,3-dimethyl-5-ethyl-1,8-octanediisocyanate, 2-methyl-4,6,8,10-tetrapropyl-1,12-dodecanediisocyanate and the like, and mixtures thereof. Additional examples of diisocyanates that are also suitable include aromatic diisocyanates, for example, 4,4'-methylenebis(phenyl isocyanate), 2,4-tolylene diisocyanate, 2,6-tolylene diisocyanate, 1,4-phenyl diisocyanate, 1,5-naphthalene diisocyanate, 1,3-bis(isocyanatormethyl)benzene, 1,3-bis(isocyanato-1-methylethyl)benzene, 1,3-bis (isocyanatomethyl)cyclohexane, bitolylene diisocyanate, 1,4-xylylene diisocyanate and the like, and mixtures thereof.

Examples of diols useful for making urethane pre-oligomers of the invention include 1,4-butanediol, 1,6-hexanediol, 1,10-decanediol, 1,9-decanediol, 1,12-dodecanediol, 1,14-tetradecanediol, 2,5-dimethyl-2,5-hexanediol, hydrogenated bisphenol A, bisphenol A, propoxylated bisphenol A, ethoxylated bisphenol A, bis (2-hydroxyethyl) terepthalate, and mixtures thereof.

Examples of ethylenically unsaturated monomers useful for reaction with the urethane pre-oligomers include methacrylates and/or acrylates. Among these include 2-hydroxyethyl methacrylate, 2-hydroxyethyl acrylate, 2-hydroxypropyl methacrylate, 3-hydroxypropyl methacrylate, hydroxypropyl acrylate, glycerol dimethacrylate, glycerol monomethacrylate, 2hydroxyethyl acrylate, hydroxypropyl acrylate, 4-hydroxybutyl methacrylate, 4-hydroxybutyl acrylate, 2-hydroxy-3-phenoxypropyl acrylate, 2-hydroxycyclohexyl methacrylate, caprolactone 2-(methacryloylox) ethyl ester, pentaerythritol triacrylate, 2-hydroxycyclohexyl acrylate and mixture thereof.

In preferred embodiments, third polymerizable acrylic compounds of the invention include difunctional methacrylates comprising reaction products of bisphenol A propoxylate, 1,6-diisocyanatohexane and 2-hydroxyethyl methacrylate; reaction products of bisphenol A propoxylate, trimethyl-1,6-diisocyanatohexane and 2-hydroxyethyl methacrylate (TBDMA); a series of reaction products of bisphenol A, trimethyl-1,6-diisocyanatohexane and 2-hydroxylethyl methacrylate; a series of reaction products of bisphenol A, 1,6-diisocyanatohexane and 2-hydroxylethyl methacrylate; a series of reaction products of trimethyl-1,6-diisocyanatohexane, 2,5-dimethyl-2,5-hexanediol and 2-hydroxyethyl methacrylate; a series of reaction products of trimethyl-1,6-diisocyanatohexane, 1,6-diisocyanatohexane, 2,5-dimethyl-2,5-hexanediol and 2-hydroxyethyl methacrylate; a series of reaction products of trimethyl-1,6-diisocyanatohexane, 1,6-diisocyanatohexane, bisphenol A propoxylate and 2-hydroxyethyl methacrylate; caprolactone 2-(methacryloyloxy)ethyl ester, and derivatives of the above compounds.

A preferred urethane dimethacrylate oligomer according to the invention can be prepared as disclosed below in Example 7.

Resin-Modifying Particle Component

Compositions of the invention also may include one or more resin-modifying particle components. These resin-modifying particle components may be dispersed in fluid resin compositions of the invention, preferably forming homogeneous colloidal dispersions or suspensions with the aforementioned polymerizable components. In an embodiment, one or more resin-modifying particles may be included in an amount of at least about 2%, preferably at least about 3%, and more preferably at least about 4%, by weight of the total composition of the invention, and no more than about 18%, preferably no more than about 15%, by weight of the total composition. By including at least about 2% by weight of resin-modifying particles in compositions of the invention, final cured resin impact strength and/or fracture toughness properties can be substantially improved in comparison to compositions where resin-modifying particles are either included in amounts less than about 2%, or excluded entirely. However, when more than about 18% by weight of resin-modifying particles are included in compositions of the invention, fluid resin composition mixing, material handling, and/or printing/curing properties may also change substantially. Thus, increasing viscosity of these fluid resin compositions could prompt further considerations. These additional considerations may include achieving homogeneous dispersion, wetting, and stable suspension of the resin-modifying particles, and/or attaining more desirable printing/curing times or print quality, and/or achieving more desirable post-print clean-up or processing results for printed articles. Therefore, in some embodiments, it may be preferable to limit inclusion of resin-modifying particles to no more than about 18% by weight of the total composition.

Resin-modifying particles comprised of organic or organic-inorganic hybrid materials may be used in particular. Organic resin-modifying particles such as poly(methyl methacrylate) (PMMA), highly crosslinked PMMA beads, poly(methyl/ethyl methacrylate), poly(methyl/butyl methacrylate), rubber modified PMMAs, core-shell impact modifiers, crosslinked polyacrylates, thermoplastic and crosslinked polyurethanes, polyethylenes, polypropylenes, polycarbonates, polyesters, polyepoxides, polystyrenes, polyamides, and the like can be used. Organic-inorganic hybrid materials, such as those derived from silicones or polyorganosiloxanes in particular, may also be used. Examples of such organic-inorganic hybrid materials may include highly crosslinked silicone resins, silicone elastomers/rubbers, and core-shell grafted (silicone elastomer core-silicone resin shell) versions. The selection of resin-modifying particle type(s) for a given composition may be made based on various considerations for achieving desired results in the fluid resin composition and/or final cured product. For example, such considerations may include, but are not necessarily limited to, inherent physical properties of particles (e.g., particle size, porosity/surface area, material density, material hardness/durometer), and the relative degree/intensity of particle inertness or interactivity (e.g., chemical compatibility or affinity) with the polymerizable components selected for the composition.

In an embodiment, resin-modifying particles may be included in the form of small particles having average diameters of at least about 0.01 microns, and no more than about 100 microns. Preferably, particles may have average diameters of at least about 0.02 microns, and no more than about 20 microns. More preferably, particles may have average diameters of at least about 0.05 microns, and no more than about 10 microns.

In some embodiments, the use of one or more core-shell type impact modifiers as a resin-modifying particle component, either alone or in combination with other non-core-shell type resin-modifying particles, may be preferred.

As used herein, the term core-shell impact modifier may denote an impact modifier wherein a substantial portion (e.g., greater than 30%, 50%, 70% or more by weight) thereof is comprised of a first polymeric material (i.e., the first or core material) that is substantially fully encapsulated by a second polymeric material (i.e., the second or shell material). These first and second polymeric materials, as used herein, can be comprised of one, two, three or more polymers that are combined and/or reacted together (e.g., sequentially polymerized), or may be part of separate or same core-shell systems. Core-shell impact modifiers can be formed by emulsion polymerization followed by coagulation or spray drying.

The first and second polymeric materials of the core-shell impact modifier can include elastomers, polymers, thermoplastics, copolymers, other components, or combinations thereof. In preferred embodiments, the first polymeric material, the second polymeric material or both of the core-shell impact modifier include or are substantially entirely composed (e.g., at least 70%, 80%, 90% or more by weight) of one or more thermoplastics. Exemplary thermoplastics include, without limitation, polycarbonate, polyester, polyolefin, polystyrene polypropylene, polyethylene terephthalate, polyvinyl chloride, polyimide, polyethylene, polybutylene terephthalate, mma-butadiene-styrene resin (MBS), acrylonitrile-butadiene-styrene resin (ABS), polymethyl methacrylate, or the like, and/or any combinations thereof. Silicone-based and silicone-acrylic-based rubber and/or butadiene-based rubber (e.g., MBS or ABS) core-shell impact modifiers may be included to further improve high impact strength and/or weatherability of cured resins.

In some embodiments, the core-shell impact modifier may be formed of, or at least include, a core-shell graft copolymer. The first or core polymeric material of the graft copolymer may have a glass transition temperature substantially (e.g., greater than 10° C., 20° C., or even 40° C.) below the glass transition temperature of the second or shell polymeric material. Moreover, it may be desirable for the glass transition temperature of the first or core polymeric material to be below 23° C. (e.g., below 10° C.), while the glass transition temperature of the second or shell polymeric material to be above 23° C., though it is to be understood this is not a required feature.

Examples of useful core-shell graft copolymers are those where typically "hard/rigid" polymeric compounds, such as styrene, acrylonitrile or methyl methacrylate, are grafted onto the exterior core of typically "soft/compressible" elastomeric or rubbery polymeric compounds, such as silicone, butadiene, or butyl acrylate. The core polymer may also include other copolymerizable compounds, such as styrene, vinyl acetate, methyl methacrylate, isoprene, or the like. The core polymer material may also include a crosslinking monomer having two or more nonconjugated double bonds of approximately equal reactivity, such as ethylene glycol diacrylate, butylene glycol dimethacrylate, and the like. The core polymer material may also include a graft linking monomer having two or more nonconjugated double bonds of unequal reactivity.

Non-limiting examples of core-shell impact modifiers that have been found to be particularly advantageous in compositions of the invention include impact modifiers available from Mitsubishi Chemical (e.g., METABLEN™ C (butadiene rubber), METABLEN™ W (acrylic rubber), and METABLEN™ S (silicone-acrylic composite rubber)), Arkema (e.g., CLEARSTRENGTH® MBS impact modifiers), and Kaneka (e.g., KANE ACE® MBS, acrylic, and specialty impact modifiers). In particular, examples of some of the preferred rubber impact modifiers may include METABLEN™ C-223A, C-201A, S-2006, S-2001, S-2030, SRK200A, and E-870A; CLEARSTRENGTH® 320, 223, D440, E920, and E950; and KANE ACE® M-211, M-570, FM-41, MR01, MR02, B-522, B-564, B-626, B-632, B-636, B637, M-511, M-731, and M-732.

In another embodiment, resin-modifying particles comprised of inorganic materials may be used. These inorganic materials may be naturally-occurring or synthetic, and may include, but are not limited to, silica, titanium dioxide, zirconium oxide, iron oxides, silicon nitrides, glasses such as calcium, lead, lithium, cerium, tin, zirconium, strontium, barium, alumino-silicates, and alumino-fluorosilicate-based glasses, borosilicate glasses, strontium borosilicate, barium silicate, lithium silicate, lithium alumina silicate, kaolin, quartz, and talc. In some embodiments, compositions including resin-modifying particles comprised of organic materials, comprised of organic-inorganic hybrid materials, and/or comprised of inorganic materials may be used in combination together to achieve desirable photopolymerizable resin composition characteristics for printing and/or final cured resin strength and durability.

Photopolymerization Initiator Component

The printable polymerizable dental compositions of this invention may include one or more photopolymerization initiator components to cause the compositions to polymerize and harden promptly and efficiently. Photopolymerizable dental compositions preferably include a light sensitizer, for example camphorquinone, 2,4,6-trimethylbenzoyl diphenylphosphine oxide (TPO), or methyl benzoin which causes polymerization to be initiated upon exposure to activating wavelengths of light, and/or a reducing compound, for example tertiary amine. The photopolymerization initiator component may be present in an amount of at least about 0.1% by weight, and preferably at least about 0.3% by weight of the total composition. The total composition may include less than about 10%, and preferably less than about 5%, by weight of the initiator component. For example, the initiator component may be present in a range of about 0.1% to about 10%, and preferably from about 0.3% to about 5% by weight of the total composition.

In one embodiment, a photoactive agent such as, for example, benzophenone, benzoin and their derivatives, or alpha-diketones and their derivatives may be added to the composition in order to make it light-curable. A preferred photopolymerization initiator is camphorquinone (CQ). Cationic polymerization initiators, diaryliodonium and triaryl sulfonium salts, such as 4-octyloxy-phenyl-phenyl iodonium hexafluoroantimonate (OPPI), can also be used, which initiates ring opening polymerization as well as volume expansion from phase change to reduce the polymerization shrinkage. Electron-transfer photosensitizers, such as polynuclear aromatic compounds, their substituted analogues, carbazoles, phenothiazines, curcumin, and titanium-complex free radical initiator can also be added. In addition, various UV light initiators can also be used. Photopolymerization can be initiated by irradiating the composition with blue, visible light preferably having a wavelength in the range of about 350 nm to about 500 nm. The camphorquinone (CQ) compounds have a light absorbency maximum of between about 400 nm to about 500 nm and generate free radicals for polymerization when irradiated with light having a wavelength in this range. Photoinitiators selected from the class of acylphosphine oxides can also be used. These compounds include, for example, monoacyl phosphine oxide derivatives, bisacyl phosphine oxide derivatives, and triacyl phosphine oxide derivatives. For example, 2,4,6-trimethylbenzoyl diphenylphosphine oxide (TPO) can be used as the photopolymerization initiator.

In addition to the photopolymerization initiator component, compositions of this invention may include a polymerization inhibitor such as, for example, butylated hydroxytoluene (BHT), hydroquinone, hydroquinone monomethyl ether, benzoquinone, chloranil, phenol, butyl hydroxyanaline (BHA), tertiary butyl hydroquinone (TBHO), tocopherol (Vitamin E), and/or others known to those skilled in the art. Preferably, butylated hydroxytoluene (BHT) is used as a polymerization inhibitor. Polymerization inhibitors act as scavengers to trap free radicals in the composition and to extend shelf life of the composition. In an embodiment, 0% up to about 0.5% by weight of one or more polymerization inhibitors may be included in compositions of the invention.

Additional Components

Depending on the intended specific dental product application and/or end-use performance properties desired, one or more of the following additional components also may be included, alone or in combination, in compositions of the invention.

Photopolymerizable compositions of this invention may further contain one or more pigments as coloring or shading agents. Mixtures of pigments may be used in order to produce various tooth-colored and gingiva-colored prosthetic or restorative articles that are aesthetically desirable and pleasing to dental practitioners and their patients. Pigment materials, in comparison to soluble dyes, are typically more desirable to use because they generally provide reliable color stability over time and good ability to withstand UV light irradiation without color degrading. Pigments may include inorganic pigments and organic pigments, and pigment particles may have their surfaces treated or modified to increase dispersibility and promote greater compatibility with liquid components of the composition. For example, inorganic pigments can be surface-treated with various materials (e.g., an organic compound, silane or silicone compound, reactive coupling agent, surfactant, or polymer) to improve bonding between the particles and resin matrix, as well as to enhance ease of dispersion in printable fluid compositions. Any of the various known methods for effectively dispersing particles/powders into liquids may be used to disperse pigments into photopolymerizable compositions of this invention.

Examples of inorganic pigments include, but are not limited to, iron oxide (e.g., black, yellow, red, brown), ultramarine blue, titanium dioxide, zinc oxide, aluminum oxide, silicone dioxide, talc, barium sulfate, calcium sulfate, cobalt chrome green, Armenian blue, carbon black, mica, cobalt violet, molybdenum red, titanium cobalt green, molybdate orange, and the like. Examples of organic pigments include, but are not limited to, Cromophtal Red-BRN 2-napthalenecarboxamide, azo pigments, polyazo pigments, azomethine pigments, isoindoline pigments, anthraquinone pigments, phthalocyanine pigments, benzimidazolone pigments, and the like.

In another embodiment, resin particle-based pigment systems may also be considered for use by encapsulating various pigments within fine polymerized resin beads (e.g., preferably less than about 20 microns). These resin beads can be prepared by emulsion or suspension polymerizations. Alternatively, highly pigment-concentrated resins (e.g., MMA-based resins) can be initially polymerized/cured, further processed by grinding into fine powders, and then subsequently dispersed in polymerizable liquid compositions.

Other optional additive agents, such as one or more antimicrobial agents, antifungal agents, rheology modifying agents, optical brightening agents, and/or fluorescing agents, may be included to impart additional complementary properties to compositions of the invention. Such optional additive agents known in the art may be selected and used insofar as they do not severely impair or adversely impact photopolymerization or curing of compositions of the invention. These optional additive agents may be included from 0% up to no more than about 5% by weight of the total composition.

Physical Properties of Uncured (Fluid) and Cured (Solid) Resin Compositions

In consideration of factors such ease of handling and use (e.g., pouring/dispensing, more complete emptying from storage container), as well as desirable "printability" attributes (e.g., rate/speed and quality/accuracy of printing) across a variety of light-based and/or material jetting systems, it may be preferable in some embodiments of the invention for uncured (fluid) resin compositions to have a viscosity of no more than about 50,000 cP (50 Pa-s) at 25° C. In other embodiments, it may be even more preferable for uncured resin compositions to have a viscosity of no more than about 30,000 cP (30 Pa-s), and further still more preferable to have a viscosity of no more than about 15,000 cP (15 Pa-s), at 25° C.

Furthermore, it can be appreciated that another desirable objective for embodiments of this invention is to achieve polymeric compositions possessing durable, strong, and tough physical property characteristics in their final cured/hardened form. Providing cured resin materials of reliable strength and toughness enables more effective use, especially in long-term dental prosthetic and restorative articles, where high resistance to both repeated impact forces and abrasion are sought. Thus, in preferred embodiments, cured resin compositions of the invention may further possess at least one, or more preferably a combination, of particular physical properties indicative of such strength and toughness. More specifically, it is possible to use known instruments and techniques for static mechanical analysis, dynamic mechanical analysis (DMA), and/or thermomechanical analysis (TMA) to quantitatively characterize solid material strength for resistance to deformation or breaking. One such preferred approach is the mechanical property testing outlined in ISO 20795-1:2013 "Dentistry—Base polymers—Part 1: Denture base polymers." In addition, it also may be possible to ascertain an indication of wear resistance properties for cured resin materials using one or more of the in-vitro techniques outlined, in ISO/TS 14569-2:2001 "Dental materials—Guidance on testing of wear—Part 2: Wear by two- and/or three-body contact." For example, one such approach utilizes the so-called Alabama (Leinfelder-Suzuki) wear simulator as a three-body cyclic abrasion wear machine. A version of this machine and methodology may be used to determine a localized wear value based on volume loss of material ($mm^3$ over 400,000 cycles at 37° C.) as one such in-vitro method to provide indication of material wear performance for occlusal surfaces under in-vivo clinical conditions.

In a preferred embodiment, cured (solid) resin compositions of the invention may have at least one, or more preferably a combination, of the following mechanical properties using additively manufactured (3D-printed) test specimen bars that are prepared and then measured according to ISO 20795-1:2013: a Flexural Stress value of at least about 90 MPa and no more than about 300 MPa, more preferably a Flexural Stress value of at least about 100 MPa and no more than about 250 MPa; a Flexural Modulus value of at least about 2300 MPa and no more than about 6000 MPa, more preferably a Flexural Modulus value of at least about 2500 MPa and no more than about 5000 MPa; a Fracture Toughness, or Maximum Stress Intensity Factor, value ($K_{max}$) of at least about 0.90 MPa-$m^{1/2}$ and no more than about 3.0 MPa-$m^{1/2}$, more preferably a Fracture Toughness value ($K_{max}$) of at least about 1.00 MPa-$m^{1/2}$ and no more than about 2.5 MPa-$m^{1/2}$; a Work of Fracture value ($W_f$) of at least about 90 $J/m^2$ and no more than about 500 $J/m^2$, more preferably a Work of Fracture value ($W_f$) of about 100 J/m$^2$ and no more than about 400 J/m$^2$. Within the context of embodiments of this invention, it is to be understood that all such mechanical property values described above are to be based on an average of at least five measured test specimens, though more specimens may be tested to further improve accuracy and precision.

In another preferred embodiment, cured resin compositions of the invention may have a Localized Wear Volume Loss value, when additively manufactured samples are prepared and then measured in accordance with the In-Vitro Localized Wear method (described further below in the Examples), of no more than about 0.15 mm$^3$ (400,000 cycles at 37° C.), more preferably a Localized Wear Volume Loss value of no more than about 0.12 mm$^3$ (400,000 cycles at 37° C.). Within the context of embodiments of this invention, it is to be understood that all such Localized Wear Volume Loss values described above are to be based on an average of at least four measured test specimens.

Resin Composition Preparation, Printing and Post-Printing Processing

Fluid resin compositions of the invention can be prepared by combining and mixing the different components together using a variety of known processing equipment and systems for blending liquids and solids together to form homogeneous mixtures. Depending on various considerations of the form and, nature of specific ingredients selected for inclusion (e.g., solid softening point or melting point temperature, particle size of materials), it is generally advantageous to prepare compositions of the invention in processing equipment or systems that are versatile for both temperature control and mixing/dispersing intensity. For example, it can be desirable in some embodiments for such equipment or systems to be capable of heating and sustaining materials for prolonged periods at temperatures substantially above ambient (25° C.) temperature (e.g., greater than 50° C., or even greater than 70° C.). Moreover, the use of high-intensity fluid shearing or dispersive systems can be particularly advantageous for ensuring more rapid and complete wetting and dispersion of resin-modifying particle components, and/or other non-soluble solid particle components (e.g., pigments). The order in which various components of the invention are introduced or combined together for processing is not particularly limited, unless otherwise specifically noted in the description of this invention.

Three-dimensional (3D) printing of resin compositions of the invention may be accomplished by a variety of known photopolymerization methods and systems. Without intending to be limiting, prepared fluid resin compositions can be loaded into programmable digitally-controlled light-based curing systems, such as SLA or DLP-based additive manufacturing systems ("vat photopolymerization"), and/or material jetting systems (e.g., inkjet, MultiJet/PolyJet printing systems), where virtual designs of custom or bespoke artificial teeth and other dental prosthetic or restorative articles can be formed in a progressive layer-by-layer, dropwise, or continuous photocuring manner. Systems that can effectively accommodate use across a broad range of fluid resin viscosity/rheology properties may be especially advantageous in allowing a greater breadth of composition variations within the scope of this invention.

In a non-limiting manner, suitable printing process parameters may be determined and selected by those skilled in the art so that a given fluid photopolymerizable resin composition may be effectively photocured in accordance with a virtual design model of a dental prosthetic or restorative article. Effectively photocuring the fluid photopolymerizable resin composition results in rapid cross-linking and hardening of the polymeric composition in-situ to form a solid structure according to the virtual design model. Effective photocuring may be accomplished with either partial curing (i.e., limited, or incomplete cross-linking and hardening) or full curing (i.e., complete, or essentially complete, cross-linking and hardening) of the polymeric composition by the 3D printing system.

A post-printing wash treatment on printed articles to remove unreacted or residual fluid photopolymerizable resin composition from surfaces of the printed prosthetic or restorative article is typically beneficial. A post-printing wash treatment may be performed by immersing the printed article in a liquid solvent composition (e.g., $C_1$-$C_3$ alcohol or other organic solvent mixture) for a brief period of time (e.g., typically for between about 1 minute and about 20 minutes). Suitable solvent compositions may be chosen by those skilled in the art to provide good miscibility and solvency properties for diluting and removing residual, unreacted resin from printed articles without being detrimental to the integrity of the printed article. Immersion may also be accompanied by sonication, mixing, jetting, spinning, or other similar means of fluid agitation to further facilitate residual resin removal from printed article surfaces.

A secondary curing treatment on printed articles may also be beneficial. Although the initial printing (photocuring) forms an initial solid prosthetic or restorative article, this secondary curing treatment can be further beneficial for ensuring complete conversion and cross-linking of the polymeric composition to fully realize the final mechanical properties and biocompatibility profile desired for patient use. In this secondary curing procedure, printed articles may be exposed to broad-spectrum electromagnetic radiation across wavelengths from about $10^{-8}$ m (10 nanometers) to $10^{-3}$ m (1 millimeter). Typically, the duration of exposure may last for between about 5 minutes and about 30 minutes across all surfaces of the printed article. Exposure to broad-spectrum electromagnetic radiation in the ultraviolet (UV) and visible wavelength ranges may be preferred. An ECLIPSE® PROCESSING UNIT (Model No. 9494800:120 Volts, 12 Amps, 1200 Watts; available from Dentsply Sirona, Inc.) is one example of a commercially available light curing device that may be used to perform a secondary curing treatment such as this. In some embodiments, such secondary curing procedures may be accompanied by the application or generation of heat to printed articles to further accelerate the final curing process.

EXAMPLES

Example 1

Preparation of a Urethane Monomer (UCDPHMA)

A 500 mL flask was charged with 97.0 grams (0.499 mol) of 1,3-bis(isocyanatomethyl)cyclohexane under dry nitrogen flow and heated to about 60° C. under positive nitrogen pressure. To this reaction mixture, 6 drops of catalyst dibutyltin dilaurate were added. A mixture of 66.2 grams (0.509 mol) of 2-hydroxyethyl methacrylate, 72.9 grams (0.505 mol) of hydroxypropyl methacrylate and 0.36 grams of butylated hydroxytoluene (BHT) as an inhibitor were added over a period of one hour while the reaction temperature was maintained between 60° C. and 80° C. After about six hours stirring, the heat was turned off, and monomer was collected from the flask as viscous liquid and stored in a dry atmosphere.

Example 2

Preparation of a Urethane Monomer (UCDPMAA)

A 500 mL flask was charged with 38.8 grams (0.200 mol) of 1,3-bis(isocyanatomethyl)cyclohexane under dry nitrogen flow and heated to about 60° C. under positive nitrogen pressure. To this reaction mixture, 3 drops of catalyst dibutyltin dilaurate were added. A mixture of 22.7 grams of 2-hydroxy-3-phenoxy propyl acrylate, 26.6 grams (0.204 mol) of 2-hydroxyethyl methacrylate, 11.5 grams (0.099 mol) of 2-hydroxyethyl acrylate and 0.10 grams of BHT as an inhibitor were added over a period of 70 minutes while the reaction temperature was maintained between 56° C. and 78° C. After about four hours stirring, the heat was turned off, and monomer was collected from the flask as viscous liquid and stored in a dry atmosphere.

Example 3

Preparation of a Urethane Monomer (UCDPPA)

A 500 mL flask was charged with 38.8 grams (0.200 mol) of 1,3-bis(isocyanatomethyl)cyclohexane under dry nitrogen flow and heated to about 60° C. under positive nitrogen pressure. To this reaction mixture, 3 drops of catalyst dibutyltin dilaurate were added. A mixture of 29.2 grams (0.203 mol) of 2-hydroxypropyl methacrylate, 22.2 grams (0.100 mol) of 2-hydroxy-3-phenoxypropyl acrylate, 11.9 grams (0.102 mol) of 2-hydroxyethyl acrylate and 0.16 grams of BHT was added over a period of 50 minutes while the reaction temperature was maintained between 66° C. and 76° C. After about 4 hours and 25 minutes stirring under 78° C., the heat was turned off, and monomer was collected from the flask as viscous liquid and stored in a dry atmosphere.

Example 4

Preparation of a Urethane Resin

A 250 mL flask was charged with 19.4 grams (0.10 mol) of 1,3-bis(isocyanatomethyl)cyclohexane under dry nitrogen flow and heated to about 48° C. under positive nitrogen pressure. To this reaction mixture, 2 drops of catalyst dibutyltin dilaurate were added. A mixture of 10.5 grams (0.047 mol) of 2-hydroxy-3-phenoxypropyl acrylate and 18.6 grams (0.143 mol) of 2-hydroxyethyl methacrylate containing 0.055 grams of BHT as an inhibitor was prepared and added over a period of one hour and 25 minutes while the reaction temperature was maintained between 65° C. and 75° C. After the addition of 90% above mixture, 1.9 gram (0.013 mol) of UNOXOL™ Diol (from Dow Chemical Company, Midland, MI) was added before the final addition of remaining 10% above mixture. UNOXOL™ Diol is a cycloaliphatic diol that is composed of approximately a 1:1 ratio of (cis, trans)-1,3-cyclohexanedimethanol and (cis, trans)-1,4-cyclohexanedimethanol. After about another 5 hours stirring, the heat was turned off, and monomer was collected from the flask as viscous colorless liquid and stored in a dry atmosphere.

Example 5

Preparation of a Urethane Monomer (UCDPMA)

A 250 mL flask was charged with 19.4 grams (0.100 mol) of 1,3-bis(isocyanatomethyl)cyclohexane under dry nitrogen flow and heated to about 60° C. under positive nitrogen pressure. To this reaction mixture, 2 drops of catalyst dibutyltin dilaurate were added. A mixture of 21.9 grams (0.168 mol) of 2-hydroxyethyl methacrylate, 7.5 grams (0.034 mol) of 2-hydroxy-3-phenoxypropyl acrylate and 0.05 grams of BHT was added over a period of 30 minutes while the reaction temperature was maintained between 62° C. and 76° C. After about 4 hours and 35 minutes stirring under 78° C., the heat was turned off, and monomer was collected from the flask as viscous liquid and stored in a dry atmosphere.

Example 6

Preparation of a Urethane/Urea Resin

A 250 mL flask was charged with 19.4 grams (0.10 mol) of 1,3-bis(isocyanatomethyl)cyclohexane under dry nitrogen flow and heated to about 64° C. under positive nitrogen pressure. To this reaction mixture, 2 drops of catalyst dibutyltin dilaurate were added. A mixture of 10.5 grams (0.047 mol) of 2-hydroxy-3-phenoxypropyl acrylate and 16.15 grams (0.139 mol) of 2-hydroxyethyl acrylate containing 0.05 grams of BHT as an inhibitor was prepared and added over a period of one hour and 25 minutes while the reaction temperature was maintained between 64° C. and 75° C. After the addition of 90% above mixture, 1.6 gram (0.014 mol) of 1,2-diaminocyclohexane was added before the final addition of remaining 10% above mixture. After about another 5 hours stirring, the heat was turned off, and monomer was collected from the flask as viscous yellow tint liquid and stored in a dry atmosphere.

Example 7

Preparation of a Urethane Dimethacrylate Oligomer (TBDMA)

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under a positive nitrogen pressure. To this reaction mixture, 10 drops of catalyst dibutyl tin dilaurate were added. The temperature of the reaction mixture was maintained between 65° C. and 140° C. for about 70 minutes and followed by additional 10 drops of catalyst dibutyl tin dilaurate. A viscous paste-like isocyanate end-capped intermediate product was formed and stirred for 100 minutes.

To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

Examples 8 to 23

For purposes of the following examples, compositions were prepared in a similar manner according to the following generalized procedure. All component materials, with the exception of the resin-modifying particle component(s), were combined together in a suitable size mixing vessel. These materials were heated and mixed to 85° C. until all materials were fully melted and homogeneously blended together into a uniform mixture (typically for at least 20-30 minutes after observing all the solid polymerizable materials to be melted). A combination of low-shear mixing (e.g., with anchor blade agitator) and high-shear dispersion (e.g., with high-speed rotor-stator mixer) was observed to be particularly effective and efficient. While continuing mixing, temperature of the mixture was then reduced and maintained at 65±5° C., at which point the resin-modifying particle component(s) were introduced to the mixture. Once the resin-modifying particle component(s) were introduced, additional low-shear mixing and high-shear dispersion were applied until the resin-modifying particles were effectively wetted and fully dispersed (typically at least 30-45 minutes). Finished mixtures of fluid resin compositions were allowed to cool and stored at ambient temperature (typically 20-25° C.) for at least 24 hours before measuring viscosity, or used in printing.

After preparation of fluid resin compositions was completed, multiple test specimen samples were printed on CARBON® M1 or M2 printers (available from Carbon, Inc.). For mechanical property testing in particular, Flexural Strength (Stress, Modulus) and Fracture Toughness ($K_{max}$, Work of Fracture) test specimen bars were printed in order to meet the dimensional specifications outlined in ISO 20795-1:2013. On the CARBON® M1 and M2 printers, printing process parameters were provided for a resin curing dosage ($D_c$), or dosage to cure, of 5.0 to 8.0 (e.g., 6.4), a resin absorption coefficient ($\alpha$) of 0.0012 to 0.0022 (e.g., 0.0017), and exposure compensation (EC) of 1 to 4 (e.g., 2.5). Additionally, a slice thicknesses of 100 microns was selected for slicing the 3D digital models of test specimen samples for printing.

Following removal of printed test specimen samples from printer, specimens were placed in glass containers having isopropanol (99%) to submerge each specimen. With lid secured to container, they were placed in ultrasonic water bath for an initial cleaning/wash cycle. An initial ultrasonic cleaning cycle of two minutes was performed, followed by removal of isopropanol from container and refilling container with fresh isopropanol to complete an additional one-minute ultrasonic cleaning cycle. Cleaned specimens were removed from containers and dried with compressed air before proceeding to a secondary curing process in an ECLIPSE® PROCESSING UNIT (Model No. 9494800; 120 Volts, 12 Amps, 1200 Watts; available from Dentsply Sirona, Inc.). Cleaned specimens were further cured for 10 minutes on each of the two largest sides of the specimen to further ensure complete resin curing for full mechanical property development.

Evaluation of viscosity for uncured fluid resin compositions was performed using a Brookfield DV2T Cone/Plate Viscometer (Brookfield Engineering Labs, Inc.) with an appropriate spindle (e.g., CPA-52Z) for the relevant viscosity range. Reported values were determined at 25±1° C. using an average of at least three (3) sample measurements.

Evaluation of mechanical properties for printed and cured solid test specimen bars was performed using an Instron® Model 3365 Universal Testing Machine (using Bluehill® Universal software) equipped with a 100 lbf (500 N) Instron Load Cell and 37±1° C. water bath according to procedures outlined in ISO 20795-1:2013. Reported mechanical property values were determined using an average of at least five (5) printed test specimen bars.

Evaluation of wear resistance properties for printed and cured solid test specimens was performed under an In-Vitro Localized Wear method, herein described below, using a customized version of the Alabama (Leinfelder-Suzuki) wear simulator. Using custom stainless steel specimen holders (each having a cylindrical cavity of 14-15 mm diameter, 4 mm depth), suitable sized portions of printed test specimen bars (stored for at least 24 hours after curing) were securely mounted in place using a self-curing acrylic base material filled into the holder cavity. Each specimen was wet polished flat using a sequence of wettable sanding papers (400, 600, 1200, 2400, and 4000 grit). Final wet-polished specimens were rinsed clean with deionized water prior to wear simulation. The assembly was mounted into a circulating water bath fixture in the wear simulator, and a tight-fitting brass cylinder collar used around each specimen holder to create a reservoir for holding an abrasive slurry. An abrasive slurry was prepared from spherical PMMA polymer beads (CAS No. 9011-14-7, unplasticized) having average particle size of about 60 μm in diameter (e.g., Polymer 68-168 (HG-5) from Dentsply Sirona, Inc.) dispersed in deionized water (polymer beads 62.5% by weight of slurry). Each test specimen within the collars remained covered in excess slurry throughout testing to maintain abrasive media. Localized wear was produced using a 3/16-inch stainless steel hardened ball bearing antagonist mounted in stylus fixture attached to a spring-loaded piston. The stylus fixture applied load onto the specimen using a 76.5±1 N (7.8±0.1 kgf) load at a rate of approximately 1 Hz. During the loading process the stylus rotated 30° as the maximum load was achieved, and then counter-rotated as the piston moved to its original position. Each specimen was subjected to 400,000 cycles at 37±1° C. Following wear simulation, specimen holders (with specimens) were submerged in a container of mild detergent-containing water (e.g., diluted liquid dishwashing detergent), then placed in an ultrasonic cleaning water bath for 10 minutes, and rinsed clean with deionized water. After allowing specimen and sample holder to dry, each specimen surface was profiled with a Keyence VHX-6000 Series Digital Microscope system (Keyence Corporation of America) to measure depth and diameter of localized wear region. Localized Wear Volume Loss ($mm^3$) was then calculated for each specimen using these depth and diameter values. Reported Localized Wear Volume Loss values were determined using an average of four (4) test specimens.

TABLE 1A

Example Compositions of the Invention

| Component | Ex. 8 (wt. %) | Ex. 9 (wt. %) | Ex. 10 (wt. %) | Ex. 11 (wt. %) |
| --- | --- | --- | --- | --- |
| Urethane Monomer - UCDPMAA (see Example 2) | 50.00 | 50.00 | 50.00 | 50.00 |
| Urethane Dimethacrylate Oligomer - TBDMA (see Example 7) | 7.00 | 7.00 | 7.50 | 7.50 |
| Ethoxylated(2) Bisphenol A Dimethacrylate | | | | |
| Ethoxylated(6) Bisphenol A Dimethacrylate | 17.50 | 17.50 | 27.00 | 13.00 |
| Trimethyloylpropane Tri(meth)acrylate | | 16.00 | | |

TABLE 1A-continued

Example Compositions of the Invention

| Component | Ex. 8 (wt. %) | Ex. 9 (wt. %) | Ex. 10 (wt. %) | Ex. 11 (wt. %) |
|---|---|---|---|---|
| Trimethyloylpropane Triacrylate | 16.00 | | | |
| 3,3,5 Trimethylcyclohexyl Methacrylate | | | | 10.00 |
| Ethylene Glycol Dimethacrylate | | | 10.00 | 10.00 |
| MBS copolymer resin (Kane Ace ® M-731) | 8.00 | 8.00 | 4.00 | 8.00 |
| 2,4,6-trimethylbenzoyl diphenylphosphine oxide | 0.98 | 0.98 | 0.98 | 0.98 |
| BHT | 0.02 | 0.02 | 0.02 | 0.02 |
| Pigments | 0.50 | 0.50 | 0.50 | 0.50 |
| Evaluations | | | | |
| Viscosity, cP at 25° C. | 25,773 | 30,717 | 6,972 | 7,805 |
| Flexural Stress, MPa (Std. Dev.) | 97 (2.2) | 102 (1.1) | 102 (2.0) | 104 (0.9) |
| Flexural Modulus, MPa (Std. Dev.) | 2563 (80) | 2608 (35) | 2682 (57) | 2656 (40) |
| $K_{max}$, MPa-m$^{1/2}$ (Std. Dev.) | 1.18 (0.06) | 1.16 (0.09) | 1.32 (0.12) | 1.25 (0.10) |
| Work of Fracture, $W_f$, J/m$^2$ (Std. Dev.) | 138 (16) | 124 (20) | 162 (29) | 151 (29) |
| Localized Wear Volume Loss, mm$^3$ (Std. Dev.) | 0.079 (0.023) | 0.089 (0.020) | 0.133 (0.039) | 0.100 (0.010) |

TABLE 1B

Example Compositions of the Invention

| Component | Ex. 12 (wt. %) | Ex. 13 (wt. %) | Ex. 14 (wt. %) | Ex. 15 (wt. %) |
|---|---|---|---|---|
| Urethane Monomer - UCDPMAA (see Example 2) | 50.00 | 57.00 | 57.00 | 57.00 |
| Urethane Dimethacrylate Oligomer - TBDMA (see Example 7) | 7.50 | 7.50 | 7.50 | 7.50 |
| Ethoxylated(2) Bisphenol A Dimethacrylate | | | | 10.00 |
| Ethoxylated(6) Bisphenol A Dimethacrylate | 17.00 | | | |
| Dipentaerythritol Pentaacrylate | | 10.00 | | |
| 3,3,5 Trimethylcyclohexyl Methacrylate | 10.00 | 20.00 | 20.00 | 20.00 |
| Ethylene Glycol Dimethacrylate | 10.00 | | 10.00 | |
| MBS copolymer resin (Kane Ace ® M-731) | 4.00 | 4.00 | 4.00 | 4.00 |
| 2,4,6-trimethylbenzoyl diphenylphosphine oxide | 0.98 | 0.98 | 0.98 | 0.98 |
| BHT | 0.02 | 0.02 | 0.02 | 0.02 |
| Pigments | 0.50 | 0.50 | 0.50 | 0.50 |
| Evaluations | | | | |
| Viscosity, cP at 25° C. | 3,754 | 27,713 | 6,245 | 19,740 |
| Flexural Stress, MPa (Std. Dev.) | 107 (0.8) | 117 (5.3) | 119 (8.6) | 115 (1.3) |
| Flexural Modulus, MPa (Std. Dev.) | 2840 (60) | 2963 (58) | 2997 (76) | 2892 (58) |
| $K_{max}$, MPa-m$^{1/2}$ (Std. Dev.) | 1.09 (0.05) | 1.07 (0.11) | 1.17 (0.10) | 1.22 (0.07) |
| Work of Fracture, $W_f$, J/m$^2$ (Std. Dev.) | 107 (15) | 93 (20) | 114 (22) | 133 (13) |
| Localized Wear Volume Loss, mm$^3$ (Std. Dev.) | 0.117 (0.032) | 0.137 (0.037) | 0.126 (0.045) | 0.117 (0.019) |

Tables 2A and 2B below provide examples of comparative compositions prepared and evaluated in the same manner as the example compositions of the invention described above.

TABLE 2A

Example Comparative Compositions

| Component | Ex. 16 (wt. %) | Ex. 17 (wt. %) | Ex. 18 (wt. %) | Ex. 19 (wt. %) |
|---|---|---|---|---|
| Urethane Monomer - UCDPMAA (see Example 2) | 40.00 | 40.00 | 30.00 | 30.00 |
| Urethane Dimethacrylate Oligomer - TBDMA (see Example 7) | 8.00 | 8.00 | 7.50 | 7.50 |
| 3,3,5 Trimethylcyclohexl Methacrylate | 35.42 | 35.42 | 50.92 | 40.92 |
| Poly(methyl methacrylate-co-ethylene glycol dimethacrylate), 8 μm spherical particle size | | 15.00 | | |
| MBS copolymer resin (Kane Ace ® M-731) | 15.00 | | 10.00 | 20.00 |
| 2,4,6-trimethylbenzoyl diphenylphosphine oxide | 0.98 | 0.98 | 0.98 | 0.98 |
| BHT | 0.10 | 0.10 | 0.10 | 0.10 |
| Pigments | 0.50 | 0.50 | 0.50 | 0.50 |

TABLE 2A-continued

Example Comparative Compositions

| Component | Ex. 16 (wt. %) | Ex. 17 (wt. %) | Ex. 18 (wt. %) | Ex. 19 (wt. %) |
|---|---|---|---|---|
| Evaluations | | | | |
| Viscosity, cP at 25° C. | 38,700 | 903 | 1214 | 105,000 |
| Flexural Stress, MPa (Std. Dev.) | 71 (1.4) | 98 (6.4) | 74 (1.0) | N/A |
| Flexural Modulus, MPa (Std. Dev.) | 1880 (42) | 2969 (87) | 2012 (3) | N/A |
| $K_{max}$, MPa-m$^{1/2}$ (Std. Dev.) | 1.26 (0.05) | 0.83 (0.04) | 1.17 (0.06) | N/A |
| Work of Fracture, $W_f$, J/m$^2$ (Std. Dev.) | 247 (21) | 73 (4) | 179 (19) | N/A |
| Localized Wear Volume Loss, mm$^3$ (Std. Dev.) | 0.319 (0.036) | 0.213 (0.050) | 0.293 (0.039) | N/A |

TABLE 2B

Example Comparative Compositions

| Component | Ex. 20 (wt. %) | Ex. 21 (wt. %) | Ex. 22 (wt. %) | Ex. 23 (wt. %) |
|---|---|---|---|---|
| Urethane Monomer - UCDPMAA (see Example 2) | 30.00 | 30.00 | 50.00 | 50.00 |
| Urethane Dimethacrylate Oligomer - TBDMA (see Example 7) | 3.00 | 3.00 | | 5.00 |
| 3,3,5 Trimethylcyclohexyl Methacrylate | 55.42 | 45.42 | 33.42 | 43.42 |
| Poly(methyl methacrylate-co-ethylene glycol dimethacrylate), 8 μm spherical particle size | | | | |
| MBS copolymer resin (Kane Ace ® M-731) | 10.00 | 20.00 | 15.00 | |
| 2,4,6-trimethylbenzoyl diphenylphosphine oxide | 0.98 | 0.98 | 0.98 | 0.98 |
| BHT | 0.10 | 0.10 | 0.10 | 0.10 |
| Pigments | 0.50 | 0.50 | 0.50 | 0.50 |
| Evaluations | | | | |
| Viscosity, cP at 25° C. | 461 | 60,687 | 30,147 | 434 |
| Flexural Stress, MPa (Std. Dev.) | 74 (0.6) | N/A | 73 (1.2) | 106 (8.8) |
| Flexural Modulus, MPa (Std. Dev.) | 1997 (28) | N/A | 1952 (18) | 2842 (86) |
| $K_{max}$, MPa-m$^{1/2}$ (Std. Dev.) | 1.03 (0.05) | N/A | 1.27 (0.06) | 0.68 (0.03) |
| Work of Fracture, $W_f$, J/m$^2$ (Std. Dev.) | 137 (11) | N/A | 230 (19) | 46 (4) |
| Localized Wear Volume Loss, mm$^3$ (Std. Dev.) | 0.262 (0.026) | N/A | 0.245 (0.039) | 0.176 (0.024) |

Upon examination of results obtained for the examples of Tables 1A through 2B, several observations can be made regarding some of the surprising advantages and benefits discovered from example compositions of the invention in relation to results of the comparative examples.

Referring to Tables 1A and 1B (Example Compositions of the Invention) above, all these examples had favorable "printability" behavior, resulting in good test specimens being printed without difficulty and maintaining consistent form integrity. Furthermore, desirable mechanical properties were observed across these examples demonstrating both robust strength (i.e., Flexural Stress and Flexural Modulus) and toughness (i.e., $K_{max}$ and Work of Fracture) characteristics. More specifically, Flexural Stress values of at least about 100 MPa, and Flexural Modulus values of at least about 2500 MPa were observed. Moreover, $K_{max}$ values of at least about 0.90 MPa-m$^{1/2}$, and Work of Fracture values of at least about 90 J/m$^2$ were also observed in these examples. It was additionally observed that all these example possessed low Localized Wear Volume Loss values, as a further indicator of material strength and resistance to prolonged wearing action. In particular, Localized Wear Volume Loss values of less than about 0.15 mm$^3$ were observed, with several examples even demonstrating less than about 0.10 mm$^3$ loss.

The previously described embodiments of the invention provide distinct benefits and advantages for photopolymerizable resin compositions. Compositions of the invention are both well-suited for use within additive manufacturing systems and processing conditions, and capable of satisfying the demanding physical and chemical performance qualities sought for dental prosthetic and restorative articles, especially for durable, long-term use as prosthetic teeth, restorative crowns, bridges, inlays, and the like.

It should be understood that the present invention does not require that all the preferred or advantageous features, nor all the advantages, need to be incorporated into every embodiment of the invention. Although the present invention has been described in considerable detail with reference to certain preferred versions thereof, other versions are possible within the scope the invention. Therefore, the spirit and scope of the appended claims should not be limited to the description of the preferred versions contained herein. All of the features disclosed in this specification, including any accompanying claims, abstract, and drawings, may be replaced by alternative features serving the same, equivalent, or similar purpose, unless expressly stated otherwise. Thus, unless expressly stated otherwise, each feature disclosed is one example only of a generic series of equivalent or similar features.

What is claimed is:

1. A photopolymerizable resin composition for the production and/or repair of dental prosthetic and/or restorative articles, the composition comprising:
   (a) from about 45% to about 70% by weight of one or more first polymerizable acrylic compounds, wherein the one or more first polymerizable acrylic compounds is a urethane di or multi(meth)acrylate derivative of 1,3-bis(isocyanatomethyl)cyclohexane characterized by one of the following formulas:

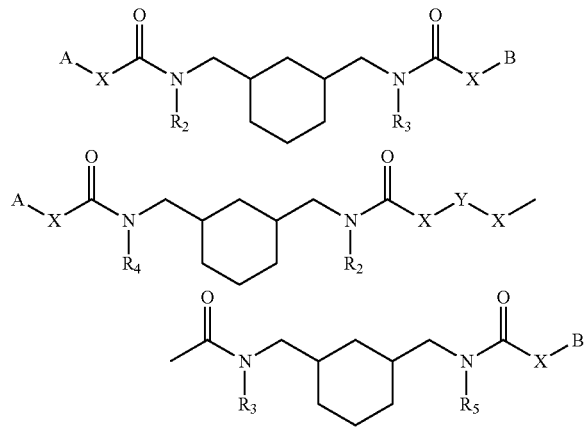

in which:
X is oxygen, nitrogen, or $NR_1$, where:
$R_1$ is hydrogen, a C1-C14 alkyl group, a C6-C14 cyclic group, C1-C14 cyclic alkyl group, a C6-C14 aromatic group, a C1-C14 aromatic alkyl group, or any combination thereof;
$R_2$, $R_3$, $R_4$ and $R_5$ is hydrogen, a C1-C14 alkyl group, a C6-C14 cyclic group, C1-C14 cyclic alkyl group, a C6-C14 aromatic group, a C1-C14 aromatic alkyl group, or any combination thereof;
Y is a C1-C14 alkyl group, a C6-C14 cyclic group, a C1-C14 cyclic alkyl group, a C6-C14 aromatic group, a C1-C14 aromatic alkyl group, or any combination thereof;
A and B independently of each other stand for one of the following formulas:

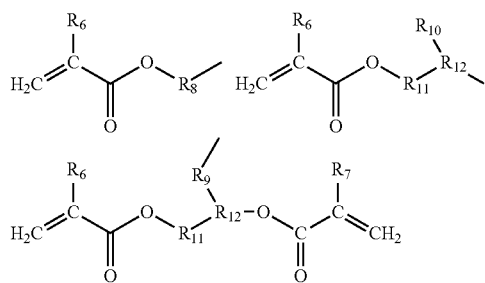

where:
$R_6$ and $R_7$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms;
$R_8$ and $R_9$ is a C1-C12 difunctional alkylene, a C1-C12 alkyl group, a C6-C12 cyclic group, a C1-C12 cyclic alkyl group, a C6-C12 aromatic group, a C1-C12 aromatic alkyl group, or any combination thereof, which can be interrupted by oxygen, sulfur, or otherwise atoms;
$R_{10}$ is hydrogen, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms;
$R_{11}$ represents a C1-C14 difunctional alkylene, a C1-C14 alkyl group, a C6-C14 cyclic group, a C1-C14 cyclic alkyl group, a C6-C14 aromatic group, a C1-C14 aromatic alkyl group, or any combination thereof, which can be interrupted by oxygen, sulfur, or otherwise atoms; and
$R_{12}$ represents a C1-C8 trifunctional alkyl group, which can be interrupted by oxygen, sulfur, or otherwise atoms;

(b) from about 15% to about 40% by weight of one or more second polymerizable acrylic compounds, the one or more second polymerizable acrylic compounds being different from the first polymerizable acrylic compounds;

(c) from about 2% to about 15% by weight of one or more third polymerizable acrylic compounds, wherein the one or more third polymerizable acrylic compounds is a methacrylate or acrylate compound prepared by reaction of a urethane pre-oligomer with an ethylenically unsaturated monomer;

(d) from about 2% to about 18% by weight of one or more resin-modifying particles, wherein the one or more resin-modifying particles is selected from the group consisting of organic core-shell impact modifiers and organic-inorganic hybrid core-shell impact modifiers; and (e) at least about 0.1% by weight of one or more photopolymerization initiators, wherein the total composition does not exceed 100% by weight.

2. The composition of claim 1, wherein the one or more third polymerizable acrylic compounds is the reaction product of a diisocyanate end-capped pre-oligomer intermediate compound with one or more hydroxyalkyl(meth)acrylate compounds.

3. The composition of claim 2, wherein the diisocyanate end-capped pre-oligomer intermediate compound is the reaction product of trimethyl-1,6-diisocyanatohexane with bisphenol A propoxylate.

4. The composition of claim 1, wherein the weight ratio of first polymerizable acrylic compound(s) ($AC_1$) to third polymerizable acrylic compound(s) ($AC_3$), $AC_1:AC_3$, is within the range of about 5:1 to about 20:1.

5. The composition of claim 1, wherein the composition comprises no more than about 10% by weight of the one or more photopolymerization initiators.

6. The composition of claim 1, further comprising at least about 0.01%, and no more than about 0.5%, by weight of one or more polymerization inhibitors.

7. The composition of claim 1, wherein the photopolymerizable resin composition has a viscosity of no more than about 50,000 cP (50 Pa-s) at 25° C. in its uncured, fluid form.

8. The composition of claim 1, wherein the photopolymerizable resin composition has a Flexural Stress value of at least about 90 MPa in its cured, solid form, using additively manufactured test specimen bars that are prepared and then measured in accordance with ISO 20795-1:2013.

9. The composition of claim 1, wherein the photopolymerizable resin composition has a Flexural Modulus value of at least about 2300 MPa in its cured, solid form, using additively manufactured test specimen bars that are prepared and then measured in accordance with ISO 20795-1:2013.

10. The composition of claim 1, wherein the photopolymerizable resin composition has a Fracture Toughness value ($K_{max}$) of at least about 0.90 MPa-m$^{1/2}$ in its cured, solid form, using additively manufactured test specimen bars that are prepared and then measured in accordance with ISO 20795-1:2013.

11. The composition of claim 1, wherein the photopolymerizable resin composition has a Work of Fracture value ($W_f$) of at least about 90 J/m$^2$ in its cured, solid form, using additively manufactured test specimen bars that are prepared and then measured in accordance with ISO 20795-1:2013.

12. The composition of claim 1, wherein the photopolymerizable resin composition has a Localized Wear Volume Loss of no more than about 0.15 mm$^3$ in its cured, solid form, using additively manufactured test specimen bars that are prepared and then measured in accordance with In-Vitro Localized Wear method.

13. The composition of claim 1, wherein the photopolymerizable resin composition has a Flexural Stress value of at least about 90 MPa, a Flexural Modulus value of at least about 2300 MPa, a Fracture Toughness value ($K_{max}$) of at least about 0.90 MPa-m$^{1/2}$, and a Work of Fracture value ($W_f$) of at least about 90 J/m$^2$ in its cured, solid form, using additively manufactured test specimen bars that are prepared and then measured in accordance with ISO 20795-1:2013.

14. The composition of claim 13, wherein the photopolymerizable resin composition has a Localized Wear Volume Loss of no more than about 0.15 mm$^3$ in its cured, solid form, using additively manufactured test specimen bars that are prepared and then measured in accordance with In-Vitro Localized Wear method.

* * * * *